United States Patent [19]

Yamazaki et al.

[11] Patent Number: 4,813,412

[45] Date of Patent: Mar. 21, 1989

[54] AUTOMATIC SYSTEM FOR AN EPILATOR DEVICE

[75] Inventors: Iwao Yamazaki; Yuji Nakamichi; Keizo Abe; Tatsuya Okudera, all of Tokyo, Japan

[73] Assignee: Ya-Man Ltd., Japan

[21] Appl. No.: 142,280

[22] PCT Filed: Dec. 27, 1983

[86] PCT No.: PCT/JP83/00459

§ 371 Date: Aug. 7, 1984

§ 102(e) Date: Aug. 7, 1984

[87] PCT Pub. No.: WO84/02461

PCT Pub. Date: Jul. 5, 1984

Related U.S. Application Data

[63] Continuation of Ser. No. 642,687, Aug. 7, 1984, abandoned.

[30] Foreign Application Priority Data

Dec. 28, 1982 [JP]  Japan ............................ 57-195907
Jul. 14, 1983 [JP]  Japan ............................ 58-126870

[51] Int. Cl.4 .................................................. A61B 17/36
[52] U.S. Cl. ................................................... 128/303.13
[58] Field of Search ............ 128/303.1, 303.13–303.17

[56] References Cited

U.S. PATENT DOCUMENTS

| 2,299,162 | 10/1942 | Marick | 128/399 |
| 3,307,554 | 3/1967 | Thornton et al. | 128/400 |
| 4,140,109 | 2/1979 | Savic et al. | 128/303.1 |
| 4,167,187 | 9/1979 | Biagi | 128/303.13 |
| 4,352,357 | 10/1982 | Caparro | 128/303.13 |
| 4,498,474 | 2/1985 | Chalmers et al. | 128/303.13 |
| 4,531,524 | 7/1985 | Mioduski | 128/303.13 |
| 4,566,454 | 1/1986 | Mehl et al. | 128/303.13 |

Primary Examiner—Max Hindenburg
Attorney, Agent, or Firm—Kane, Dalsimer, Sullivan, Kurucz, Levy, Eisele and Richard

[57] ABSTRACT

This invention relates to an automatic system for beauty equipment of eternal epilation, facial treatment, beautiful skin creation, weight reduction, etc. This system provides the measuring apparatuses (1, 2, 3, 4, 5, 6, 7) that measure the condition of the portion to which beauty treatment is to be applied, e.g. skin moisture, temperature, pH, etc. It processes the output obtained through the above measuring apparatuses by central processing unit (11, 12, 13, 14) in operation and then controls the operating condition of beauty equipment (22, 23, 24, 25), e.g. strength or weakness of the output, on or off, based on the above result.

12 Claims, 6 Drawing Sheets

AUTOMATIC SYSTEM FOR AN EPILATOR DEVICE

RELATED APPLICATION

This application is a continuation of co-pending U.S. patent application Ser. No. 642,687, filed Aug. 7, 1987, abandoned Dec. 30, 1987.

TECHNICAL FIELD

This invention relates to an automatic system for beauty treatment that decides the operating conditions of various beauty equipments. It activates metabolism (replacing the old with the new) through stimulation of skin by applying an electromagnetic wave of an infrared ray or laser. This system includes an eternal epilator to remove unwanted hair by applying, etiher separately or in combination, direct current voltage, high frequency output or laser beam.

BACKGROUND TECHNIQUE

When performing eternal epilation or other beauty treatments, changing or setting up of various conditions is required, depending on the condition of the hair or skin to be treated. Previously, these conditions have been decided according to the treatment technician's experience or intuition. However, these conditions are very complicated and need full-scale measuring equipment or an analyzer based on physical or chemical principles. Therefore, setting up of suitable conditions required great skill. Especially when precise judgement had to be made on the conditions based on more than two data that were obtained by this equipment, extremely high level experience or intuition was required. Accordingly, high-level skill was required of the treatment technicians. Technicians with little experience had great difficulty in setting up conditions quickly. Also, it was not efficient to spend hours for obtaining data by measurement or interview for each eternal epilation or other beauty treatment. When performing a special treatment, a few measurement results and data from a couple of past measurements were sufficient as information sources. Yet, treatment technicians spent lots of time considering and comparing the data, or average case with the present case.

THE OBJECTIVE OF THE INVENTION

It is the principal of the present invention to provide an automatic system for beauty treatments, including eternal epilation, that makes it possible to perform eternal epilation and other beauty treatments under the best conditions by combining complicated data obtained through the hair or skin to be treated. This principal is achieved through an automatic beauty system that includes external epilation. This system is constructed as in the claim mentioned. The system characterizes itself by possessing the following: data measuring apparatuses that measure moisture, temperature, pH, etc. of the portion to be treated and operation control unit which sets and provides operating conditions needed for external epilator and other various beauty equipments based on various data from the above data measuring equipment. This automatic system for beauty treatments includes an eternal epilator that makes it possible to control various output apparatuses under the best treatment conditions. The best condition is obtained through general analysis of data obtained from a total beauty interview and the moisture. temperature, pH, skin color and elasticity, facial form, oil content of the skin of the portion to be treated. As a result, a desirable beauty treatment under the best condition is provided at any time without high-level expertise or intuition.

BRIEF DESCRIPTION OF THE DRAWINGS

FIG. (1) is a block diagram that illustrates the basics of the automatic beauty treatment system of this invention including eternal epilation.

FIG. (2) is a basic flow chart of pH measuring apparatus in FIG. (1).

Figure 1:
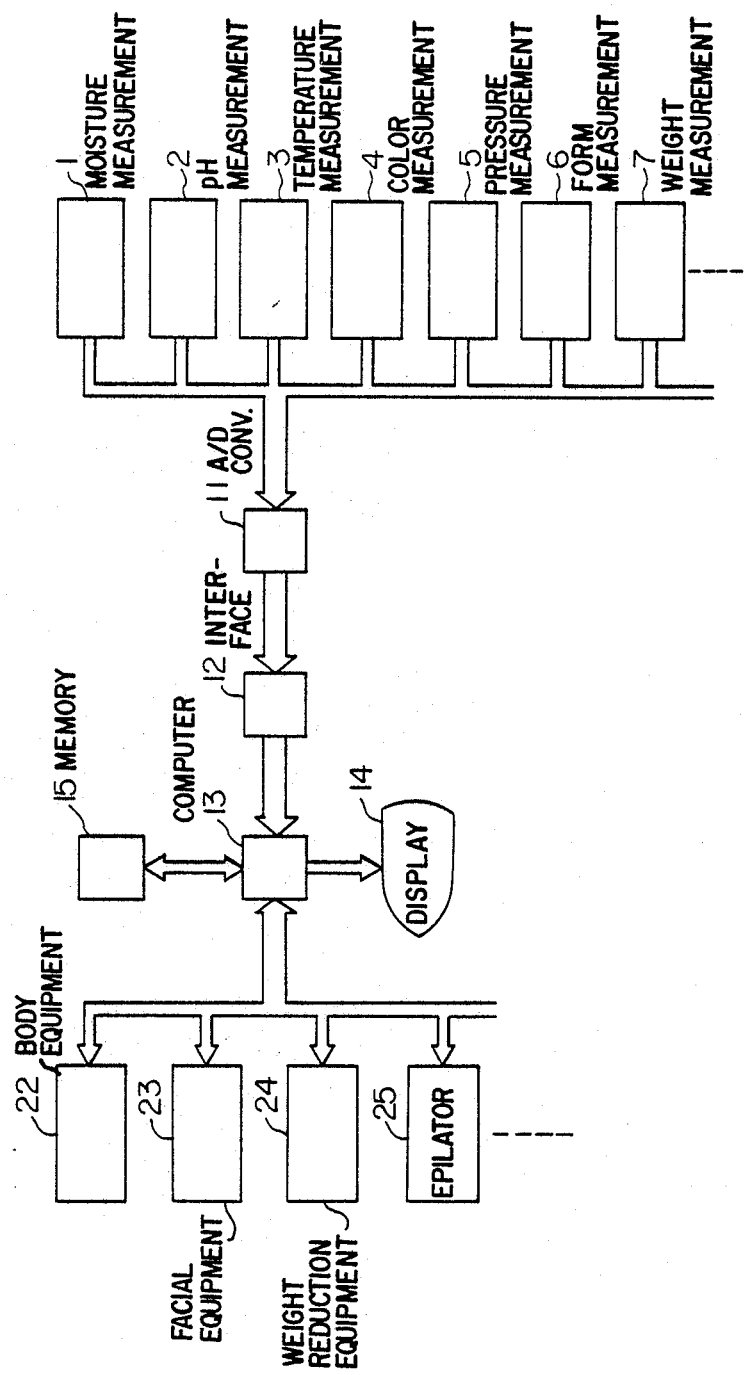
Figure 2:
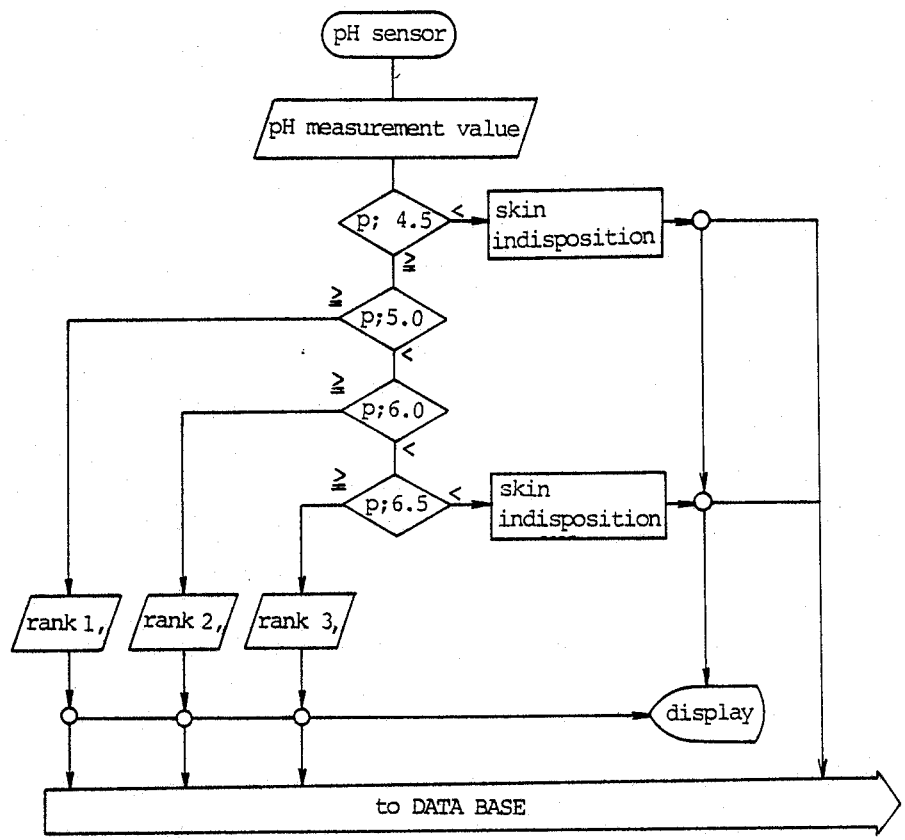
Figure 3:
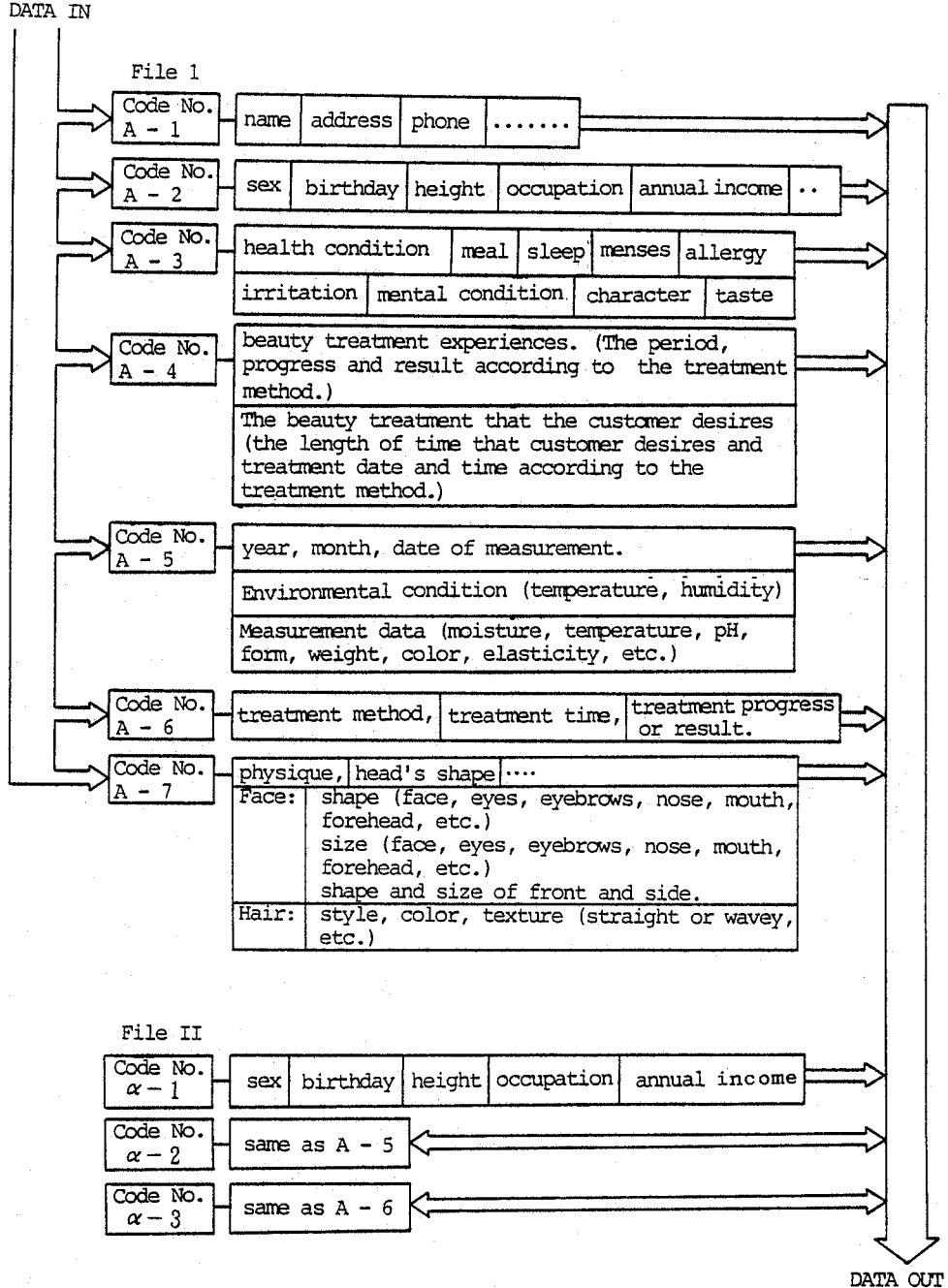
Figure 4:
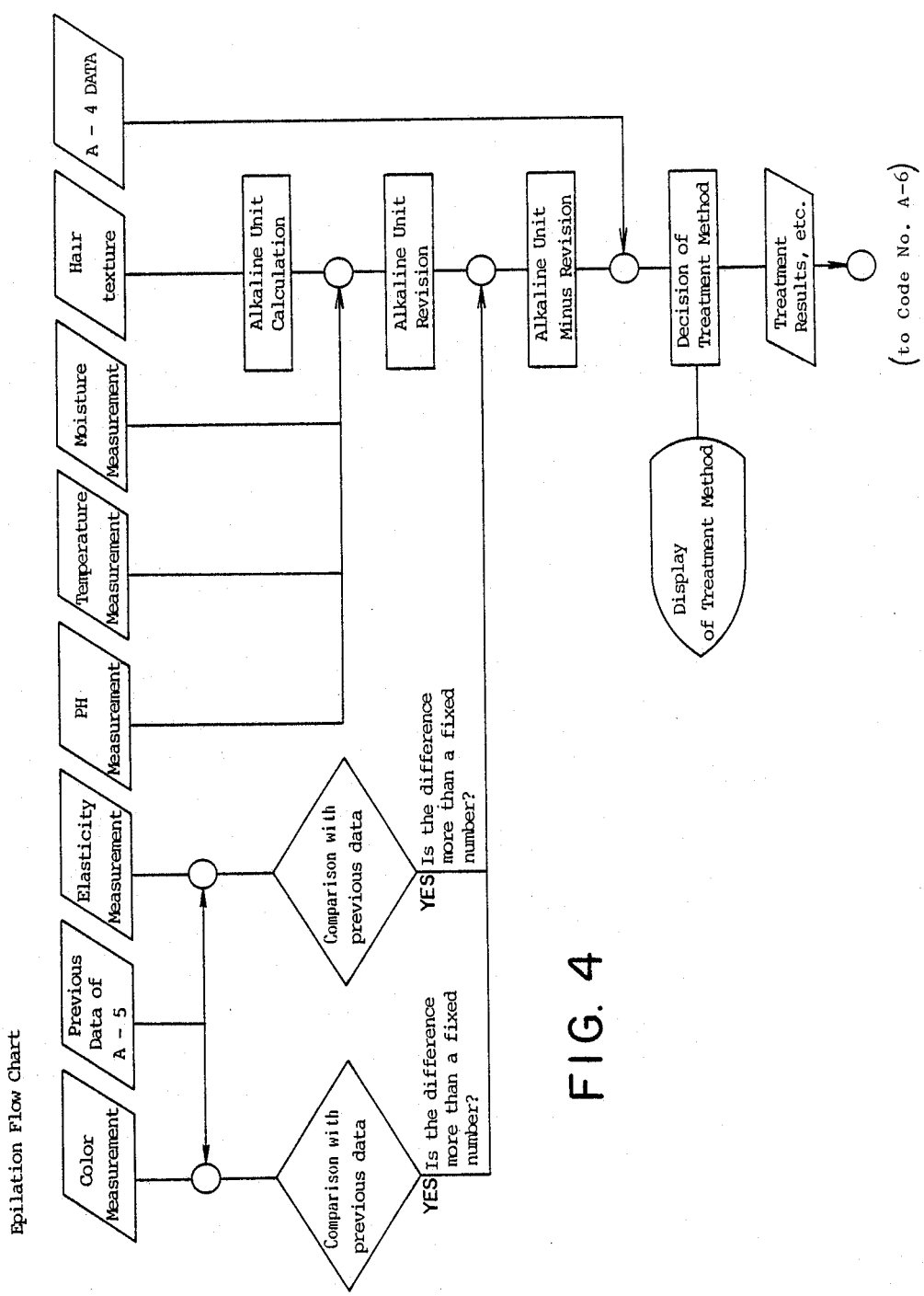
Figure 5:
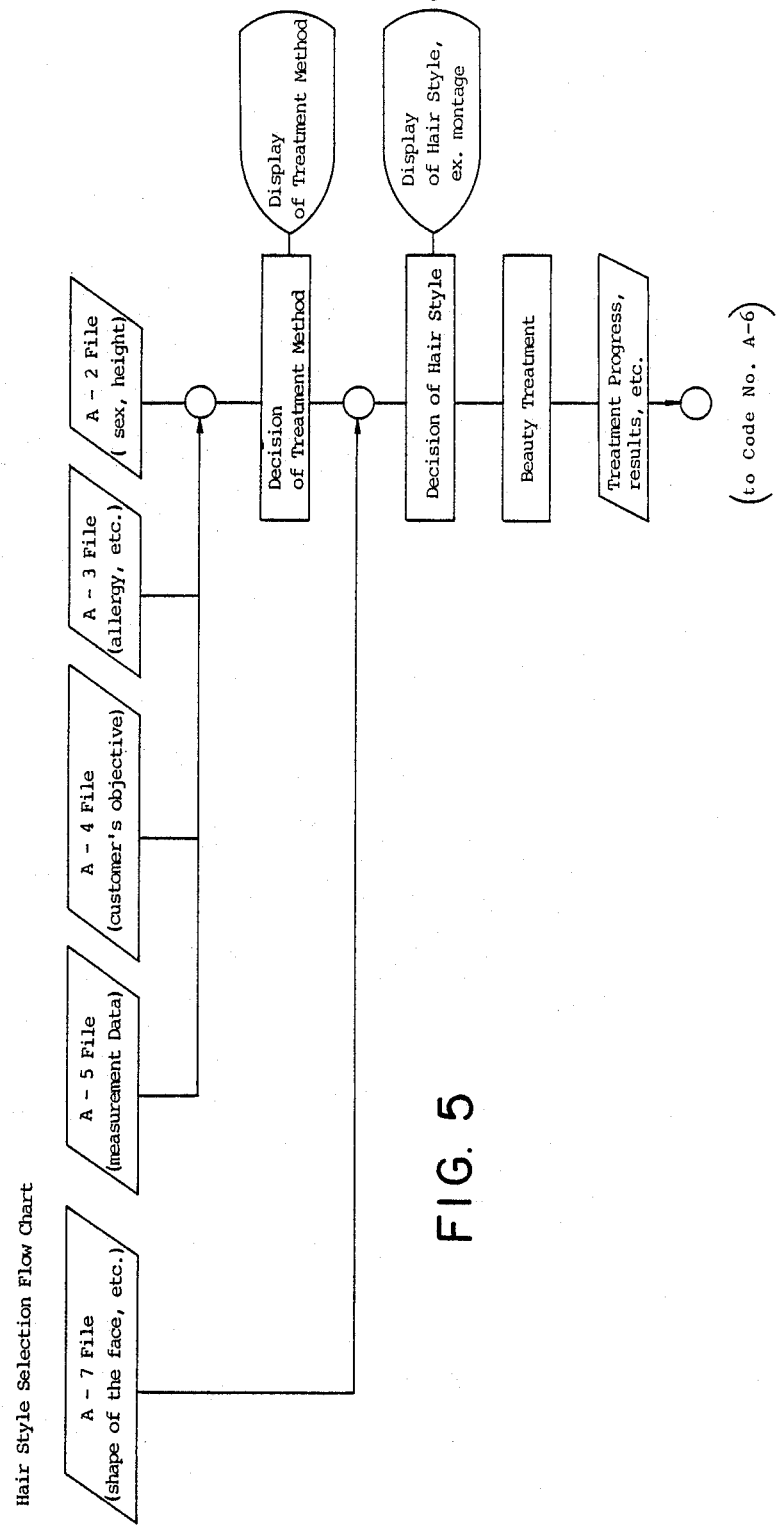
Figure 6:
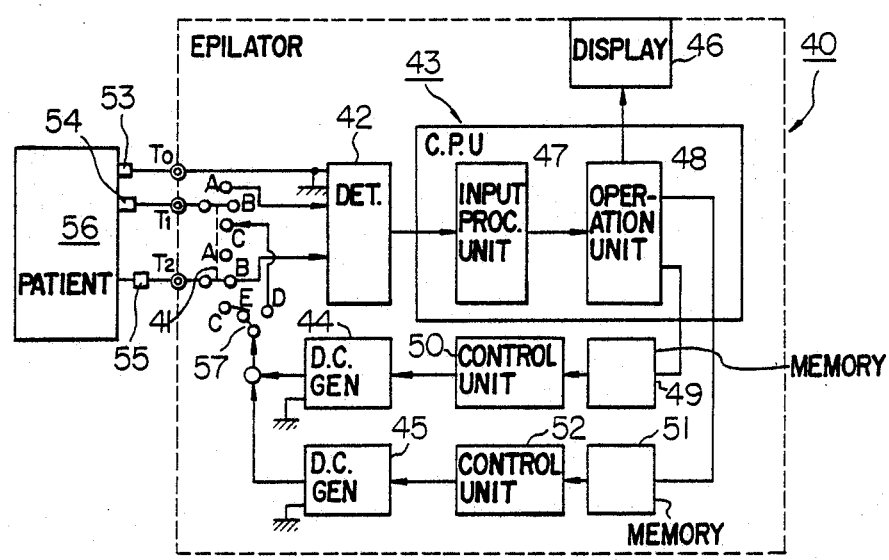

FIG. (3) is a block diagram that illustrates the outline of computer and memory part of FIG. (1).

FIG. (4) is a flow chart that illustrates basic system of eternal epilator of FIG. (1).

FIG. (5) is a selection flow chart of hair style that is a part of entire body beauty treatment of FIG. (1).

FIG. (6) is a block diagram that illustrates a working example of automatic system for beauty treatment of this invention as applied to eternal epilator.

BEST FORM FOR WORKING OF AN INVENTION

Following is a disclosure of this invention and refers to the attached illustration of a working example.

FIG. (1) illustrates construction of automatic system of this invention and consists of measuring apparatuses shown in reference marks (1) to (7), operation control unit shown in reference marks (11) to (14) and various beauty equipments shown in reference marks (22) to (25).

Various measuring apparatuses are used as measuring apparatuses (1) to (7) as occasion calls. However, in the case of eternal epilator, the objects are moisture, pH, temperature, color, elasticity of the skin and thickness of hair, etc. In compliance with these conditions, the following must be considered: whether the output of eternal epilator should be either direct current or high frequency, or both; whether they should be applied continuously or applied in a pulse-like manner; and what kind of output, i.e. big, medium, small, etc. should we use.

Following is a description of the relationship between these conditions and eternal epilation or other beauty treatments.

First, the quantity of skin's moisture effects the whole process and each treatment speed remarkably changes according to its quantity. Especially in eternal epilation, the quantity of skin moisture is so important that the relationship between eternal epilation and the quantity of skin moisture should be mentioned.

At present, general eternal epilation treatment is done by electricity. Existing epilation methods are the electrolysis patterns using direct current, high-frequency heating patterns and blend patterns which use both electrolysis patterns and high-frequency heating patterns. An eternal epilation done by using electrolysis patterns affect hair follicles by changing them to alkaline through electrolysis by moisture lying in these follicles after being applied direct current voltage to make electrode grasped in hand anode and electrode put in follicle cathode. An eternal epilation done by high-frequency heating patterns heats moisture in follicle through dielectric heating after applying high frequency as same as the one of electrolysis patterns.

The blend type eternal epilation is performed through synergistic effect by using the above combined equipment. The quantity of the skin's moisture, especially in hair follicles, greatly influences the epilation results. However, it is impossible to perceive the quantity of moisture of skin, especially in these follicles by just looking or touching by hand.

Therefore, the operation has been done depending an operator's intuition up to now. It was impossible to perform a suitable epilation that grasped the quantity of moisture in follicle because it differs by age, sex and the portion, to be exact. Thus, we have been having the problems of overtreatment or insufficient treatment. Also the range of the value of pH of normal skin is from 4.5 to 6.5 and is acidic. There is a big difference in the value between individuals and this value even varies in a same person due to the sweating or other conditions. The value of pH greatly influences each each beauty treatment condition. Furthermore, the skin temperature is important since an infrared ray irradiation, etc. are included in the weight reduction of entire body. It is recognized that what we call an acupuncture spot has a lower temperature than the other parts of the body and it is important because it helps to detect the parts to which laser irradiation is to be applied.

It is well known that cosmetics should be selected depending on the color of the skin, i.e. pale or sun-tanned. The color of the skin also greatly influences eternal epilation and other beauty treatments. Up to the present, the color of the skin has been judged inaccurately by the naked eye because of the background color or illumination. The skin elasticity is an important factor of the beauty treatment since it shows the degree of the elasticity. As a matter of fact, the value of the hair taken as a sample should be understood thoroughly and used as data because the shape and weight of the hair treated is an important factor in the treatment.

This performance is equipped with the moisture measuring apparatus (1), pH measuring apparatus (2), temperature measuring apparatus (3), color measuring apparatus (4), pressure measuring apparatus (5), form measuring apparatus (6) and weight measuring apparatus (7). It is understood that other systems can be constructed as needed. Common equipment by which an electric output is obtained based on the principle of physics or chemicals is available for the above each measuring apparatus. The following is a disclosure of the most general construction.

Moisture measuring apparatus (1) measures, for example, the moisture through the electrical resistance between the two electrodes that touch the skin. Also a humidity sensor is available.

The well known glass electrode can be used as the pH measuring apparatus (2). The glass electrode is suitable for the pH measurement of the surface of the skin. In the case that the pH measurement of the hair follicle is needed, the pH indicator can be used to the root of the treated hair.

The pH measurement by the glass electrode has several advantages, for example, the restriction of the object measured is small, continuous measurement is possible and so on, and it is adopted to Japanese Industrial Standard.

The thermoelectric couple or thermistor, which measures electromotive force or electric resistance through contact with Device Under Test, is available as the temperature measuring apparatus (3). Also, the measurement using infrared ray in non-contact is adopted.

The color sensor, which has a color filter added to the photo diode, is simply used as the color measuring apparatus (4). For example, the display is easily done by XYZ color display system (CIE*1931*XYZ color display system) or L'a'b' color display system (CIE1976*-L'a'b'*—Color Space) through the amorphous integrated circuit type color sensor or monolithic color sensor.

The electrostatic capacitance type or other types pressure sensor is available as the pressure measuring apparatus (5).

The CCD or other image sensors can be used as the form measuring apparatus (6). The digital type micrometer or slide calipers can be used, but they are not suitable for the measurement of extremely minute hairs.

A chemical beam can be used as the weight measuring apparatus (7) and the measuring value of hair should be inputted. Also, sensors that measure minute weight or mass can be used.

The operation control part consists of A/D converter (11), interface (12), computer (13) and display part (14). The parts are formed by the well-known factors. It is preferable that the display part (14) is constructed to be able to display switching of the detecting value of each measuring part, the result of operation and the operating condition of each beauty equipment which will be mentioned later.

The various beauty equipment consist of beauty equipment for the entire body (22), facial treatment (23), weight reduction equipment (24) and eternal epilator (25). Each unit employs CPU that obtains the best control with A/D converter and D/A converter and is suitable for transferring the signal between each equipment and the operation control unit.

Each beauty equipment and the main data needed by each equipment are disclosed. First, the moisture amount, temperature, pH and the hair condition(-weight) are important in an eternal epilator. Moreover, the skin color, skin elasticity and so on are important in the comparison with the previous measuring value.

In total body beauty, the moisture amount, temperature, facial form and physique are important. In a weight reduction, it is important to understand how weight, moisture amount, temperature, pH or facial form, and physique change. This data can be measured by a simple measuring apparatus employed in each beauty equipment and can be transmitted to the computer as data according to circumstances.

FIG. (2) shows a flow chart of the pH measuring apparatus (2). It indicates something wrong if the pH value is either less than 4.5 or more than 6.5 on the display unit. In this figure, the pH value between 4.5 and 6.5 is divided into three. However, it is properly added, if necessary.

FIG. (3) is a block diagram that shows the outline of the computer (13) and the memory storage part (15). Among the code numbers used here, code No. A is a part that is common in File I and code No. of another person is expressed in B. Therefore, a File I is regarded as the individual karte.

A - 1 shows the inherent data for the code No. A.

A - 2 shows data that is almost unnecessary to be changed once it is inputted.

A - 3 shows data to be filed after every measurement is performed.

A - 4 shows the basic data obtained through an interview, etc.

A - 5 shows the measuring data that is a basic for beauty treatment.

A - 6 shows data obtained through treatment performance.

A - 7 shows data that mainly relate to display.

Alpha part is a code that is common for file II as same as A and it is mainly the data base part which performs a statistic process. The value processed there is used in the comparison with other data.

FIG. (4) is a flow chart that shows the basic construction of eternal epilator. In this figure, the alkali unit number, which is a standard for treating eternal epilation, is calculated through the form of hair such as thickness or length. The alkali unit number is amended by adding factors obtained through each sensor of pH, temperature and moisture to the value calculated according to hair type (form).

Concerning the color of skin, the upper limit is set of the alkali unit or the unit number is subtracted, for example, in case where, it suddenly changes, compared with the previous measurement, because of suntan, etc., or skin elasticity suddenly changes. The result of these treatments are filed in Code No. A - 6 together with the method and process.

FIG. (5) is a flow chart that selelcted a hair style that is appropriate for total body beauty. It also selects a suitable hair style treatment (e.g. permanent wave), how to make-up, suitable cosmetics, etc.

In this automatic system according to this invention, the best condition is calculated by the operation according to the conditions obtained through each kind of the measuring apparatuses (1) to (7) previously mentioned. The beauty equipments (22) to (25) are most suitably controlled by the results of the above operation. Accordingly, it is possible to perform a safe, comfort and secure beauty treatment under the most suitable conditions at all times, regardless of operating technician's experience or intuition.

FIG. (6) specifically shows a block diagram of an eternal epilator among the objects of the automatic system for beauty treatment according to this invention and indicates the construction which omits the part of power supply of the equipment. The eternal epilator shown by the broken line (40) possesses the following: memory storage parts (49), (51), which control oscillators (44) and (45) according to the output of a changeover switch (41), detector (42), central processing operation unit (CPU) (43), high frequency generator (44), direct current generator (45) and CPU (43). It also possesses control units (50) and (52) and also possesses the displayer (46) which indicates the measurement value, if necessary. The CPU (43) consists of the input processing unit (47) and operation unit (48). Moreover, an eternal epilator (40) equips terminals for input and output, $T_0$, $T_1$ and $T_2$.

Terminal $T_0$ connects with a metal hand electrode (53), which is a common electrode of moisture measurement and eternal epilation treatment. Terminal $T_1$ connects with electrode (54) used for measuring skin moisture or pre and post-treatment of opilation. Terminal $T_2$ connects with a probe electrode (55) used for measuring moisture in follicle and for epilation. Electrodes (53), (54) and (55) are contacted and plugged in a human body (56) that needs epilation.

The following explains the operation of the eternal epilation according to this invention. It becomes possible to measure skin moisture and perform pre and post-treatment of epilation, if a changeover switch (41) matches a point of contact A. And it becomes possible to measure moisture in the hair follicle if a changeover switch matches a point of contact B. An epilation is performed under the condition that a changeover switch matches a point of contact C.

When measuring skin's moisture, an electrode (54) contacts with a part of a skin to be measured after a metal hand electrode (53) is held by a customer in his or her hand setting a changeover switch (41) to a point of contact A. After measuring the above under this condition, detector (42) detects input from a metal hand electrode (53) and an electrode (54) and then applies detected input to an input processing unit (47) in the CPU (43). The detected value is processed in operation in the operation unit (48) and displayed on the displayer (46), if necessary.

In case of measuring moisture in hair follicle, a probe electrode (55) should be plugged in follicle to be epilated after a metal hand electrode (53) is held by a customer in his or her hand setting a changeover switch (41) to a point of contact B. After measuring the above under this condition, a detector (42) detects an electric resistance between a metal hand electrode (53) and a probe electrode (55) and a detected value is processed as same as the above and then displayed on a displayer (46).

During the epilation treatment, the most suitable voltage and application time are set based on a result of each moisture measurement of the above. These controls are done through an operation unit (48) in the CPU (43) and a control operation is done by control units (50) and (52) through data stored in first and second memory storage units (49) and (51). The output of a control unit (50) controls a direct current generator (44) and the output of a control unit (52) controls a direct current generator (45). As a result, an epilation treatment is performed under the most suitable condition for the status of moisture in follicle and of skin.

A pre-(and post) treatment of an eternal epilation is done by switching an addition switch (57) to a point of contact D, setting a changeover switch (41) to a point of contact C and applying a weak voltage between a metal hand electrode (53) and an electrode (54). By performing a before treatment, the skin's pores are opened, and plugging of an epilation probe in an electrode is facilitated to thereby ensure an epilation. An after treatment of epilation is done by tightening pores through reversing of the polarity of two electrodes and neutralizing an entire part.

After a pre-treatment of epilation, a point of contact of an addition switch (57) should be set to E side remaining a changeover switch (41) as it is (a point of contact C). An epilation treatment is performed according to a combination of time set based on the previous measurement and voltage and of direct current and high frequency after plugging a tip of a probe electrode (55) in pores. This setting value is decided according to the moisture measurement value obtained just prior to an epilation treatment under the most suitable condition for the statuses of age, sex, follicle and skin. Therefore, it makes it possible to peform an appropriate epilation treatment without requiring the very high level skill since an operator's intuition is not needed.

It would be evident that much transformation and modification can be done within the range of this invention in this disclosure based on an working example of this invention.

What is claimed is:

1. An automatic system for removing unwanted hair from a patient by the application of electromagnetic wave energy from epilator means, which system comprises:
- epilator means for applying electromagnetic wave energy to a hair for conduction to the hair papilla;
- electromagnetic wave energy generating means connected to the epilator means for producing electromagnetic wave energy at a desired frequency and voltage;
- measuring means for measuring one or more physical parameters of said patient, said parameter or parameters being selected from the group consisting of skin moisture, skin pH, skin temperature, skin color, and hair weight; and
- receiving means for receiving said measurements, evaluating said measurements, and automatically determining operating conditions of said epilator means, said receiving means being connected (i) to said measuring means to receive said measurements and (ii) to said electromagnetic wave generating means to produce electromagnetic wave energy at a desired frequency and voltage.

2. The automatic system of claim 1, wherein the parameter or parameters are selected from the group consisting of skin moisture, skin pH, skin temperature, and hair weight.

3. The automatic system of claim 1, wherein the single parameter measured is skin moisture.

4. An automatic system to decide the operating conditions of an external epilator and facial treatment equipment to be applied to a patient, said epilator being adapted to remove unwanted hair by the application of electrical energy in the form of one or more of direct current, low frequency current, and high frequency current and said facial treatment equipment being adapted to activate metabolism through skin stimulation by the application of electromagnetic wave energy such as infrared rays, ultraviolet rays, laser rays and the like, said automatic system comprising:
- first means for measuring physical parameters of said patient;
- second means for calculating and evaluating alkali unit numbers based upon said physical parameters of said patient and thickness and/or length of hair; and
- third means for automatically selecting and setting the operating conditions and/or facial treatment equipment in response to said data values from said first and second means and other physical parameters of said patient.

5. The automatic system of claim 4, wherein the first means measures skin moisture, skin pH, skin temperature, and skin pressure.

6. The automatic system of claim 4, wherein the first means measures skin moisture, skin pH, and skin temperature.

7. The automatic system of claim 4, wherein said other physical parameters are skin color and skin elasticity.

8. The automatic system of claim 4 which comprises an automatic system for removing unwanted hair by application of electromagnetic energy from epilator means and for facial treatment by skin stimulation comprising:
- epilator means for applying electromagnetic wave energy to a hair for conduction to the hair papilla;
- electromagnetic wave energy generating means for producing electromagnetic wave energy at a desired frequency and voltage;
- means for measuring one or more physical parameters of the patient, said parameters or parameters being selected from the group consisting of skin moisture, skin pH, skin temperature, skin color, skin elasticity, hair thickness, and length of hair;
- receiving means for receiving said measurements;
- means for calculating and evaluating alkali unit numbers based upon said measurements; and
- receiving means for receiving said measurements, evaluating said measurements, and automatically determining operating conditions of said epilator means, said receiving means being connected to said measuring means to receive said measurements and to said electromagnetic wave generating means to produce electromagnetic wave energy at a desired frequency and voltage.

9. The automatic system of claim 4, wherein unwanted hair is removed by application of electromagnetic energy from epilator means.

10. The automatic system of claim 4, wherein facial treatment comprises skin stimulation by application of electromagnetic wave energy.

11. The automatic system of claim 4, wherein an alkali unit number is determined from measurements of one or more physical parameters selected from the group consisting of skin moisture, skin pH, skin temperature, skin color, skin elasticity, hair thickness, and length of hair.

12. An automatic system to decide the operating conditions of external epilator equipment to be applied to a patient, said epilator being adapted to remove unwanted hair by the application of electrical energy, said automatic system comprising:
- first means for measuring skin moisture, skin pH, and skin temperature;
- second means for measuring hair thickness and/or length and calculating alkali unit members;
- third means for receiving data from said first and second means and calculating revised alkali unit numbers;
- fourth means for measuring skin color and skin elasticity;
- fifth means for receiving data from said third and fourth means and calculating further revised alkali unit numbers; and
- decision means to evaluate said further revised alkali unit numbers and other data regarding the patient to automatically determine epilator operating conditions.

* * * * *